United States Patent [19]

Reich et al.

[11] Patent Number: 5,741,829
[45] Date of Patent: Apr. 21, 1998

[54] RADIATION-CURABLE ACRYLATES WITH BUILT-IN PHOTOINITIATORS

[75] Inventors: Wolfgang Reich, Maxdorf; Erich Beck, Ladenburg; Ulrich Jäger, Harthausen; Reinhold Schwalm, Wachenheim, all of Germany

[73] Assignee: BASF Aktiengesellschaft, Ludwigshafen, Germany

[21] Appl. No.: 674,832

[22] Filed: Jul. 3, 1996

[30] Foreign Application Priority Data

Jul. 7, 1995 [DE] Germany .................. 195 24 812.0

[51] Int. Cl.$^6$ .................. C08G 00/00; C07C 69/96; C08F 18/24
[52] U.S. Cl. .................. 522/35; 522/97; 522/100; 522/108; 522/905; 526/314; 558/270; 558/268
[58] Field of Search .................. 558/268, 270; 522/35, 97, 100, 108, 905; 526/314

[56] References Cited

U.S. PATENT DOCUMENTS 5,248,805 9/1993 Boettcher et al. .

FOREIGN PATENT DOCUMENTS

| 1337353 | 10/1995 | Canada . |
| 0 281 941 | 9/1988 | European Pat. Off. . |
| 0 377 191 | 7/1990 | European Pat. Off. . |

*Primary Examiner*—Johann Richter
*Assistant Examiner*—Joseph Murray
*Attorney, Agent, or Firm*—Oblon, Spivak, McClelland, Maier & Neustadt, P.C.

[57] ABSTRACT

Radiation-curable (meth)acrylates obtainable by reacting compounds of the formula

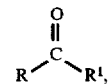

I in which R is $C_1$–$C_4$-alkyl, aryl or $R^1$ and $R^1$ is

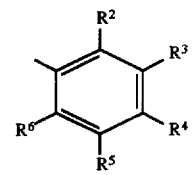

II in which $R^2$ to $R^6$ independently of one another are H, $C_1$–$C_4$-alkyl, $C_1$–$C_4$-alkoxy, OH, phenyl, SH, $SCH_3$, $SC_2H_5$, F, Cl, Br, CN, COOH, COO—($C_1$–$C_{17}$-alkyl), COO—($C_5$–$C_{10}$-aryl), $CF_3$, $N(alkyl)_2$, N(alkyl)(aryl), $N(aryl)_2$, $N^\oplus(alkyl)_3 A^\ominus$, $N^\oplus H(alkyl)_2 A^\ominus$, $A^\ominus$ is the anion of an acid, and alkyl or aryl, unless indicated otherwise, is $C_1$–$C_{10}$-alkyl or $C_5$–$C_{10}$-aryl, respectively, and at least one but not more than 3 of $R^2$ to $R^6$ are

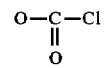

with hydroxy(meth)acrylates containing at least 1 free hydroxyl group and at least 2 (meth)acrylic groups in the molecule.

11 Claims, No Drawings

RADIATION-CURABLE ACRYLATES WITH BUILT-IN PHOTOINITIATORS

The invention relates to radiation-curable (meth)acrylates obtainable by reacting compounds of the formula

   I where R is $C_1$–$C_4$-alkyl, aryl or $R^1$ and $R^1$ is

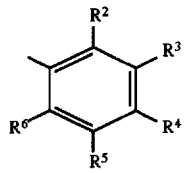   II where $R^2$ to $R^6$ independently of one another are H, $C_1$–$C_4$-alkyl, $C_1$–$C_4$-alkoxy, OH, phenyl, SH, $SCH_3$, $SC_2H_5$, F, Cl, Br, CN, COOH, COO—($C_1$–$C_{17}$-alkyl), COO—($C_5$–$C_{10}$-aryl), $CF_3$, N(alkyl)$_2$, N((alkyl)(aryl)), N(aryl)$_2$, $N^\oplus$(alkyl)$_3A^\ominus$, $N^\oplus H$(alkyl)$_2A^\ominus$, $A^\ominus$ is the anion of an acid, and alkyl or aryl, unless indicated otherwise, is $C_1$–$C_{10}$-alkyl or $C_5$–$C_{10}$-aryl, respectively, and at least one but not more than 3 of $R^2$ to $R^6$ are

with hydroxy(meth)acrylates containing at least one free hydroxyl group and at least two (meth)acrylic groups and/or acrylic groups in the molecule.

The invention additionally relates to a process for the preparation of the radiation-curable (meth)acrylates and to their use in radiation-curable compositions.

It is known to incorporate copolymerizable photoinitiators as comonomers in polymers. In this way, subsequent migration or volatilization of the photoinitiators from prepared coatings can largely be avoided.

Copolymerizable or coreactive photoinitiators are also known from EP 281 941.

EP-A-377 191 discloses copolymerizable photoinitiators which are obtainable by reacting compounds of the above formula I with monoacrylates.

A disadvantage is that monoacrylates subjected to radiation curing are often not incorporated completely into the polymer, which may lead to the unwanted escape of the photoinitiators from prepared coatings.

It is therefore an object of the present invention to provide radiation-curable (meth)acrylates of high reactivity with low proportions of extractable photoinitiators.

We have found that this object is achieved by the radiation-curable (meth)acrylates defined above, a process for their preparation, and their use in radiation-curable compositions.

The novel radiation-curable (meth)acrylates are obtainable by reacting compounds of the formula I with hydroxy (meth)acrylates containing at least one free hydroxyl group and at least two (meth)acrylic groups.

In the formula I R is preferably methyl and especially preferably is phenyl. $R^2$ to $R^6$ independently of one another are preferably H, $C_1$–$C_4$-alkyl or alkoxy or OH which is not in the ortho-position to the carbonyl, with from one to three of $R^2$ to $R^6$, preferably one of $R^2$ to $R^6$ being

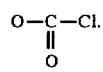

A particularly preferred compound of the formula I is

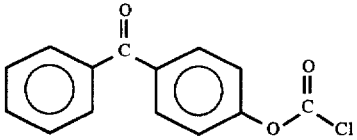   III

The aromatic chloroformates (cf. J. Prakt. Chem. 313 (1971) 331, and 317 (1975) 62, 73, 81) of the general formula I can be prepared in good yield from a substituted phenol, for example 4-chloro-5'-fluoro-2'-hydroxybenzophenone, 4-chloro-4'-hydroxybenzophenone, 2,4-dihydroxybenzophenone, 4,4'-dihydroxybenzophenone, 4-fluoro-4'-hydroxybenzophenone, 2-hydroxybenzophenone, 4-hydroxybenzophenone, 2-hydroxy-4-methoxybenzophenone, 2,3,4-trihydroxybenzophenone, 2-hydroxythioxanthone, 3-hydroxythioxanthone, 4-hydroxyphenyl 2-hydroxy-2-propyl ketone (DE-A 35 34 645) by phosgenization, using standard methods known from the literature, with phosgene, see for example Houben-Weyl, Methoden der organischen Chemie, Vol. 8, Thieme-Verlag 1952, trichloromethyl chloroformate (diphosgene), J. Prakt. Chem. 126 (1930) 210 and 128 (1930) 233, Chem. Abstr. 95, 81766, J. Org. Chem. 41 (1976) 2070 and 50 (1985) 715, Angew. Chem. 89 (1977) 267, crystalline triphosgene, Angew. Chem. 99 (1987) 922, or with N,N'-carbonyldiimidazole or N,N'-carbonyldi-s-triazole (Fieser 1 (1967) 116).

The hydroxy(meth)acrylates which can be reacted with the compound I to give the novel radiation-curable (meth)acrylates contain at least one and preferably from one to 4 hydroxyl groups, particularly preferably 1–2 hydroxyl groups. These hydroxyl groups may be in the alcohol which is esterified with the (meth)acrylic acid or else may otherwise, for example, be incorporated into the molecule by Michael addition of primary or secondary amines onto (meth)acrylic groups, especially acrylic groups, which are substituted by, for example, a hydroxyalkyl group.

They also contain at least 2, preferably from 2 to 6, particularly preferably from 2 to 4, acrylic or methacrylic groups in the molecule. The groups concerned are preferably acrylic groups, and the compounds concerned are therefore preferably hydroxyacrylates.

Examples of suitable hydroxy(meth)acrylates are trimethylolpropane diacrylate and pentaerythritol triacrylate.

Mention may also be made of epoxy acrylates as are obtainable, for example, by reacting epoxidized olefins, glycidyl esters of saturated or unsaturated carboxylic acids, or glycidyl ethers of aliphatic or aromatic polyols, with (meth)acrylic acid.

Further suitable compounds are urethane acrylates which can be prepared, for example, by reacting polyisocyanates with hydroxyl-containing (meth)acrylic esters.

Preferred hydroxy(meth)acrylates are polyester or polyether (meth)acrylates having at least one free hydroxyl group and from 2 to 6 acrylic groups, preferably 2–4 acrylic groups in the molecule.

The polyester and/or polyether (meth)acrylates can be prepared by a method known to the person skilled in the art, namely the esterification of hydroxyl-containing polyesters or polyethers using (meth)acrylic acid in such an amount that the desired number of free hydroxyl groups remains in the molecule.

The molecular weights $M_n$ of the hydroxyl-containing polyesters or polyethers is preferably between 100 and 4000 ($M_n$ determined by gel permeation chromatography).

Hydroxyl-containing polyesters of this kind can be prepared, for example, in a customary manner by esterifying dicarboxylic acids or polycarboxylic acids with polyols having at least 3 OH groups, alone or in a mixture with diols. The starting materials for such hydroxyl-containing polyesters are known to the person skilled in the art. Dicarboxylic acids which can be employed with preference are succinic acid, glutaric acid, adipic acid, sebacic acid, o-phthalic acid and the isomers and hydrogenation products thereof, and also esterifiable derivatives, such as anhydrides, for example maleic anhydride, or dialkyl esters of said acids. Polycarboxylic acids or their anhydrides which may be mentioned are triacids or tetraacids, such as trimellitic anhydride or benzenetetracarboxylic acid. Suitable diols are preferably ethylene glycol, propylene 1,2- and 1,3-glycol, 1,4-butanediol, 1,6-hexanediol, neopentyl glycol, cyclohexanedimethanol and polyglycols of the ethylene glycol and propylene glycol type. Suitable polyols are primarily trimethylolpropane, glycerol or pentaerythritol or dimers thereof, for example, sorbitol. Suitable diols or polyols are also alkoxylated (with for example ethylene oxide or propylene oxide) diols or polyols, especially those with a degree of alkoxylation of from 0 to 10, based on the respective hydroxyl groups of the diol or polyol. The polyesterols also include polycaprolactonetriols, whose preparation is likewise familiar to the person skilled in the art.

Examples of suitable hydroxyl-containing polyethers are those which can be obtained by known processes, by reacting polyhydric alcohols with various quantities of alkylene oxides, preferably ethylene oxide and/or propylene oxide.

Preference is given to alkoxylation products of the abovementioned polyols, especially those having a degree of alkoxylation of from 0 to 10, based on the respective hydroxyl groups in the polyols, although in this context at least two ether groups are present overall in the molecule.

The preparation of the novel radiation-curable (meth)acrylates is preferably carried out with the exclusion of moisture. Examples of suitable solvents are dry, nonnucleophilic solvents, such as acetonitrile, dichloromethane, dichloroethane, tetrahydrofuran, toluene, xylene, chlorobenzene, ethyl acetate and chloroform.

The reaction of the hydroxy(meth)acrylates with the chloroformates of the formula I can be carried out at from 0° to 100° C., preferably from 10° to 50° C. Where the (meth)acrylates are liquid, some or all of the solvent can be omitted.

The novel radiation-curable (meth)acrylates can be used, alone or in a mixture with other radiation-curable polymers or monomers, as radiation-curable compositions.

In the case of mixtures, the proportion of the novel acrylates should in general be at least 0.5% by weight, preferably at least 2% by weight, based on the mixture, in order to ensure adequate reactivity for the radiation curing without the addition of other photoinitiators.

Good results are obtained in particular with a content of from 2 to 40% by weight, in particular up to 20% by weight, of the novel radiation-curable acrylates, based on the radiation-curable mixture. Particularly suitable co-components for mixtures are radiation-curable (meth)acrylates such as epoxy (meth)acrylates, urethane (meth)acrylates, polyether or polyester (meth)acrylates or $C_1$–$C_{18}$-alkyl (meth)acrylates and $C_2$–$C_{18}$-alkylene di(meth)acrylates, but also monomers such as alkyl acrylates, aromatic vinyl compounds, vinyl esters, unsaturated polyesters, etc.

In the case of the novel acrylates with the abovementioned co-components it is possible for some of the (meth)acrylic groups, for example from 0 to 30 mol-%, preferably from 0.1 to 30 mol-%, particularly preferably from 0.5 to 10 mol-%, based on all of the (meth)acrylic groups, can be present in the form of Michael adducts of primary or secondary amines onto the acrylic group, whereby it is possible to increase the reactivity as regards radiation curing.

The radiation-curable compositions can be used as or in coating compositions, for example paints, printing inks or adhesives, as printing plates, as shaped articles, for the production of photoresists, in stereolithography, or as a casting composition, for example for optical lenses.

Additives can be added to the novel radiation-curable acrylates or to said mixtures when these acrylates or mixtures are used as a coating composition, examples of such additives being crosslinking agents, thickeners, leveling agents, fillers and pigments.

Radiation curing can be effected by irradiation with UV light.

EXAMPLES 1. 100 g of a polyether acrylate (Laromer® LR 8812) were admixed with 5.75 g of chloroformate of the formula III and 3.3 g of triethanolamine at room temperature. 300 ml of ethyl acetate were then added. After 2 hours, the triethanolammonium chloride formed was washed out using distilled water in a separating funnel. After removal of the aqueous phase, the ethyl acetate was distilled off. (Viscosity of the end product: 928 mPas).

2. 100 g of butanediol diglycidyl ether diacrylate were reacted with 5.75 g of chloroformate of the formula III and 3.3 g of triethanolamine at 50° C. for 2 hours. The triethanolammonium chloride formed was then separated off via a pressure filter. (Viscosity: 880 mPas).

3. The procedure was as in Example 2, but 100 g of bisphenol A diglycidyl ether diacrylate (80% strength in butyl acetate) were reacted with 5.75 g of chloroformate of the formula III and 3.3 g of triethanolamine.

4. 5 g of diethanolamine were added at 70° C. to 100 g of butanediol glycidyl ether diacrylate. After reaction for 4 hours, the mixture was cooled to 50° C. and 5.75 g of chloroformate of the formula III and 3.3 g of triethanolamine were added. After 2 hours, the ammonium salt was separated off via a pressure filter.

5. 46 g of diethanolamine were added at 70° C. to 375 g of an ethoxylated trimethylolpropane triacrylate. After a reaction period of 3 hours, the mixture was filtered and the filtrate drawn off. (Viscosity: 320 mPas).

To 100 g of this product there were added 10 g of chloroformate III, 100 g of ethyl acetate and 3.3 g of triethanolamine, and the mixture was heated to 50° C. After a reaction period of 4 h, the ammonium salt was separated off over a K7 pressure filter, and the ethyl acetate was then removed by distillation. (Product: acid number (AN): 6.0 mg of KOH/g; iodine color number (ICN): 7–10; viscosity: 660 mPas).

6. 1000 g of a polyether acrylate ((Laromer PO 33 F) were reacted with 100 g of chloroformate of the formula III and 57.3 g of triethanolamine at 55° C. for 2.5 hours. The ammonium salt is then separated off over a K10 pressure filter.

Product: AN: 8 mg of KOH/g; ICN: 10–15; viscosity: 150 Pas.

7. 175 g of diethanolamine were added to 350 g of Laromer PO 33F, and the mixture was reacted at 50°–60° C. for 4 hours. Product: AN: 0.3 mg of KOH/g; viscosity: 4.16 Pas.

100 g of this resin are mixed with 26 g of chloroformate of the formula III, 14.8 g of triethanolamine and 100 g of ethyl acetate, and the mixture is worked up as described above.

Product: AN: 33.8 mg of KOH/g; viscosity: 27.5 Pas.

Use Examples

A The product from Example 1) was applied in a thickness of 15 μm to paper and the applied coat was irradiated with a UV lamp (IST, MCX 300 1 lamp 120 W/cm). The reactivity was 35 m/min, i.e. a transportation speed of 35 m/min (coated samples are passed under the UV lamp) resulted in scratch-resistant coatings. The chemical resistance according to DIN 68 860 B was 0.95 (mean value of 10 tests).

Comparison A

For comparison purposes, 4% of benzophenone was added to the Laromer LR 8812 used in Example 1, this mixture was applied to KD paper in a thickness of 15 μm, and the applied coat was cured by means of UV irradiation. The reactivity was 35 m/min. (Chemical resistance 1.1).

B The product from Example 2 was diluted with 5% water, and the resulting mixture was applied in a thickness of 100 μm to KD paper, and the applied coat was cured by means of UV light. The reactivity was 20 m/min. The chemical resistance (mean value of 10 tests according to DIN 68 860 B) gave a rating of 1.3 (low numerical value = good chemical resistance).

Comparison B

For comparison, the butanediol diglycidyl ether diacrylate used in Example 2 was diluted with water, 4% of Irgacure® 500 was added, the mixture was applied in a thickness of 100 μm to KD paper and the applied coat was cured using UV. The reactivity was 30 m/min. The chemical resistance (mean value of 10 tests according to DIN 68 860 B) gave a rating of 2.5.

We claim:

1. A radiation-curable (meth)acrylate which is the reaction product of a compound of the formula

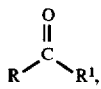

where R is $C_1$–$C_4$-alkyl, aryl or $R^1$ and $R^1$ is

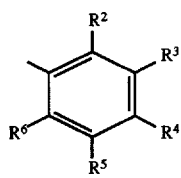

wherein $R^2$ to $R^6$ independently of one another are H, $C_1$–$C_4$-alkyl, $C_1$–$C_4$-alkoxy, OH, phenyl, SH, $SCH_3$, $SC_2H_5$, F, Cl, Br, CN, COOH, COO—($C_1$–$C_{17}$-alkyl), COO—$C_5$–$C_{10}$-aryl), $CF_3$, $N(alkyl)_2$, $N(alkyl)(aryl)$, $N(aryl)_2$, $N^{\oplus}(alkyl)_3 A^{\ominus}$, $N^{\oplus}H(alkyl)_2 A^{\ominus}$, $A^{\ominus}$ is the anion of an acid, and alkyl or aryl is $C_1$–$C_{10}$-alkyl or $C_5$–$C_{10}$-aryl, respectively, and at least one but not more than three of $R^2$ to $R^6$ are

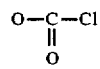

with a hydroxy(meth)acrylate which contains at least 1 free hydroxyl group and at least two (meth)acrylic groups in the molecule.

2. A radiation-curable (meth)acrylate as claimed in claim 1, wherein one of $R^2$ to $R^6$ is

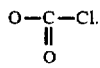

3. A radiation-curable (meth)acrylate as claimed in claim 1, wherein the hydroxy(meth)acrylate is a polyether or polyester (meth)acrylate which contains at least one free hydroxyl group and from two to six acrylic groups in the molecule.

4. A radiation-curable (meth)acrylate as claimed in claim 1, wherein the hydroxy(meth)acrylate is a polyether or polyester (meth)acrylate in which the free hydroxyl group has been incorporated into the resin via Michael adducts of the (meth)acrylic groups with alkanolamines.

5. A process for the preparation of a radiation-curable (meth)acrylate, wherein a compound of the formula I is reacted with hydroxy(meth)acrylates which contain at least one free hydroxyl group and at least two (meth)acrylic groups.

6. A radiation-curable composition comprising a radiation-curable (meth)acrylate as claimed in claim 1.

7. A radiation-curable (meth)acrylate as claimed in claim 1, wherein said compound of the formula I is

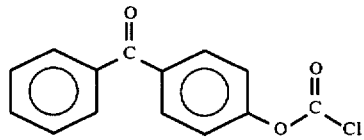

and said hydroxy(meth)acrylate is a polyether acrylate.

8. A radiation curable (meth)acrylate as set forth in claim 1, wherein said hydroxy(meth)acrylate is butanediol diglycidyl ether diacrylate.

9. A radiation curable (meth)acrylate as set forth in claim 1, wherein said hydroxy(meth)acrylate is bisphenol A diglycidyl ether diacrylate.

10. A radiation curable (meth)acrylate as set forth in claim 1, wherein said hydroxy(meth)acrylate is a polyester or polyether(meth)acrylate having at least one free hydroxy group and two to four acrylic groups in the molecule.

11. A radiation curable (meth)acrylate as set forth in claim 1, wherein R is phenyl and $R^1$ is a group of the formula II wherein $R^2$, $R^3$, $R^5$ and $R^6$ are hydrogen and $R^4$ is

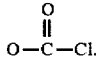

* * * * *